(12) United States Patent
Yamada et al.

(10) Patent No.: US 9,282,990 B2
(45) Date of Patent: Mar. 15, 2016

(54) TREATMENT DEVICE

(71) Applicant: OLYMPUS CORPORATION, Tokyo (JP)

(72) Inventors: Masashi Yamada, Sagamihara (JP); Norihiro Yamada, Hino (JP); Shinya Masuda, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/324,860

(22) Filed: Jul. 7, 2014

(65) Prior Publication Data

US 2014/0378971 A1 Dec. 25, 2014

Related U.S. Application Data

(63) Continuation of application No. PCT/JP2013/083168, filed on Dec. 11, 2013.

(60) Provisional application No. 61/736,806, filed on Dec. 13, 2012.

(51) Int. Cl.
*A61B 17/32* (2006.01)
*A61B 17/22* (2006.01)
(Continued)

(52) U.S. Cl.
CPC ..... *A61B 17/320068* (2013.01); *A61B 17/2202* (2013.01); *A61B 17/282* (2013.01);
(Continued)

(58) Field of Classification Search
CPC .............. A61B 17/320068; A61B 17/32009; A61B 17/2202; A61B 17/282; A61B 17/285; A61B 18/1445; A61B 2017/22015; A61B 2017/22018; A61B 2017/320076; A61N 7/00
See application file for complete search history.

(56) References Cited

U.S. PATENT DOCUMENTS 6,129,735 A   10/2000 Okada et al.
6,790,216 B1 *  9/2004 Ishikawa ................. 606/169
(Continued)

FOREIGN PATENT DOCUMENTS

JP   A-11-113922       4/1999
JP   A-2005-288024    10/2005
(Continued)

OTHER PUBLICATIONS

Jan. 21, 2014 International Search Report issued in International Application No. PCT/JP2013/083168.
(Continued)

*Primary Examiner* — Michael Peffley
(74) *Attorney, Agent, or Firm* — Oliff PLC

(57) ABSTRACT

A treatment device includes a first grip member having an elongated shape, and a second grip member which is displaced with respect to the first grip member to grip the biological tissue between the first grip member and the second grip member. The second grip member includes a grip section that comes into contact with a biological tissue as a gripping target. $I/A^2$ of the grip section is maximum at the proximal end, and/or $Z/A^{3/2}$ of the grip section is maximum at the proximal end, where I is a second moment of area, Z is a section modulus, and A is a cross-sectional area calculated based on an axis perpendicular to a straight line passing through a center of gravity of the first grip member and a center of gravity of the second grip member in a cross section perpendicular to a longitudinal axis of the grip section.

8 Claims, 16 Drawing Sheets

(51) Int. Cl.
*A61B 18/14* (2006.01)
*A61B 17/28* (2006.01)
*A61B 17/285* (2006.01)
*A61N 7/00* (2006.01)
*A61B 17/29* (2006.01)

(52) U.S. Cl.
CPC ....... *A61B17/285* (2013.01); *A61B 17/320092* (2013.01); *A61B 18/1445* (2013.01); *A61N 7/00* (2013.01); *A61B 2017/22015* (2013.01); *A61B 2017/22018* (2013.01); *A61B 2017/2825* (2013.01); *A61B 2017/2926* (2013.01); *A61B 2017/320076* (2013.01)

(56) References Cited

U.S. PATENT DOCUMENTS

| | | | |
|---|---|---|---|
| 2005/0004589 A1* | 1/2005 | Okada et al. | 606/169 |
| 2005/0049546 A1 | 3/2005 | Messerly et al. | |
| 2007/0191713 A1 | 8/2007 | Eichmann et al. | |
| 2007/0225608 A1* | 9/2007 | Houser et al. | 600/471 |
| 2009/0248051 A1* | 10/2009 | Masuda | 606/169 |
| 2011/0066174 A1* | 3/2011 | Gilbert | 606/169 |

FOREIGN PATENT DOCUMENTS

| | | |
|---|---|---|
| JP | A-2006-513737 | 4/2006 |
| JP | A-2007-268260 | 10/2007 |
| JP | A-2009-514566 | 4/2009 |
| JP | A-2009-240773 | 10/2009 |

OTHER PUBLICATIONS

Jun. 16, 2015 International Preliminary Report on Patentability issued in International Application No. PCT/JP2013/083168.

Aug. 26, 2014 Office Action issued in Japanese Application No. 2014-528780.

* cited by examiner

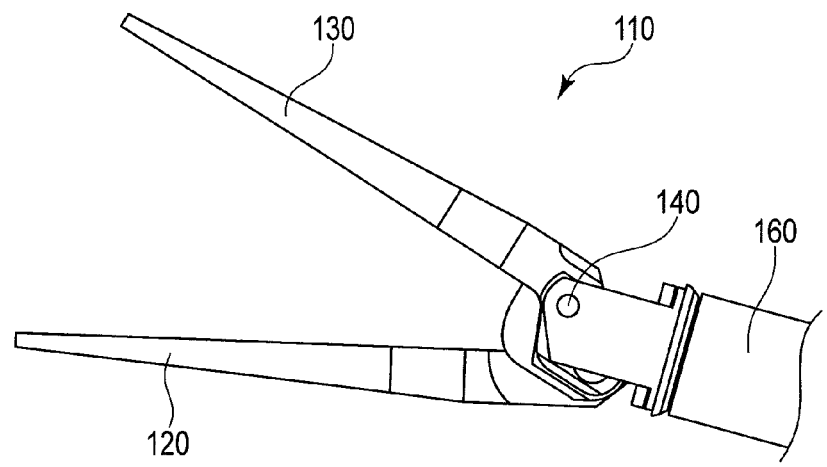
F I G. 2
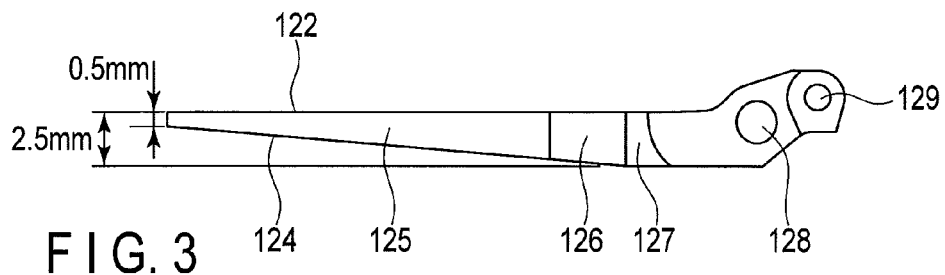
F I G. 3
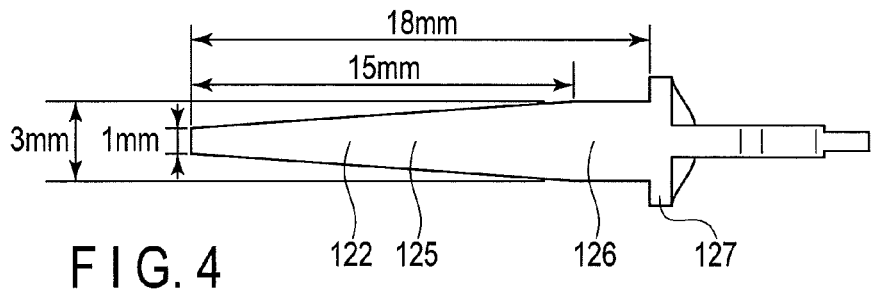
F I G. 4
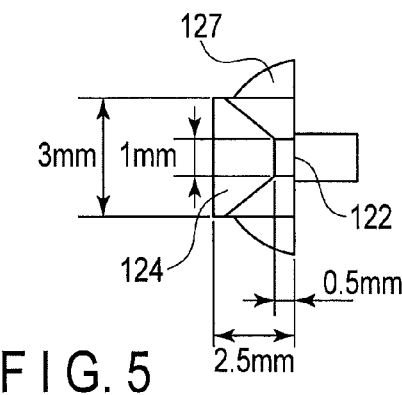
F I G. 5

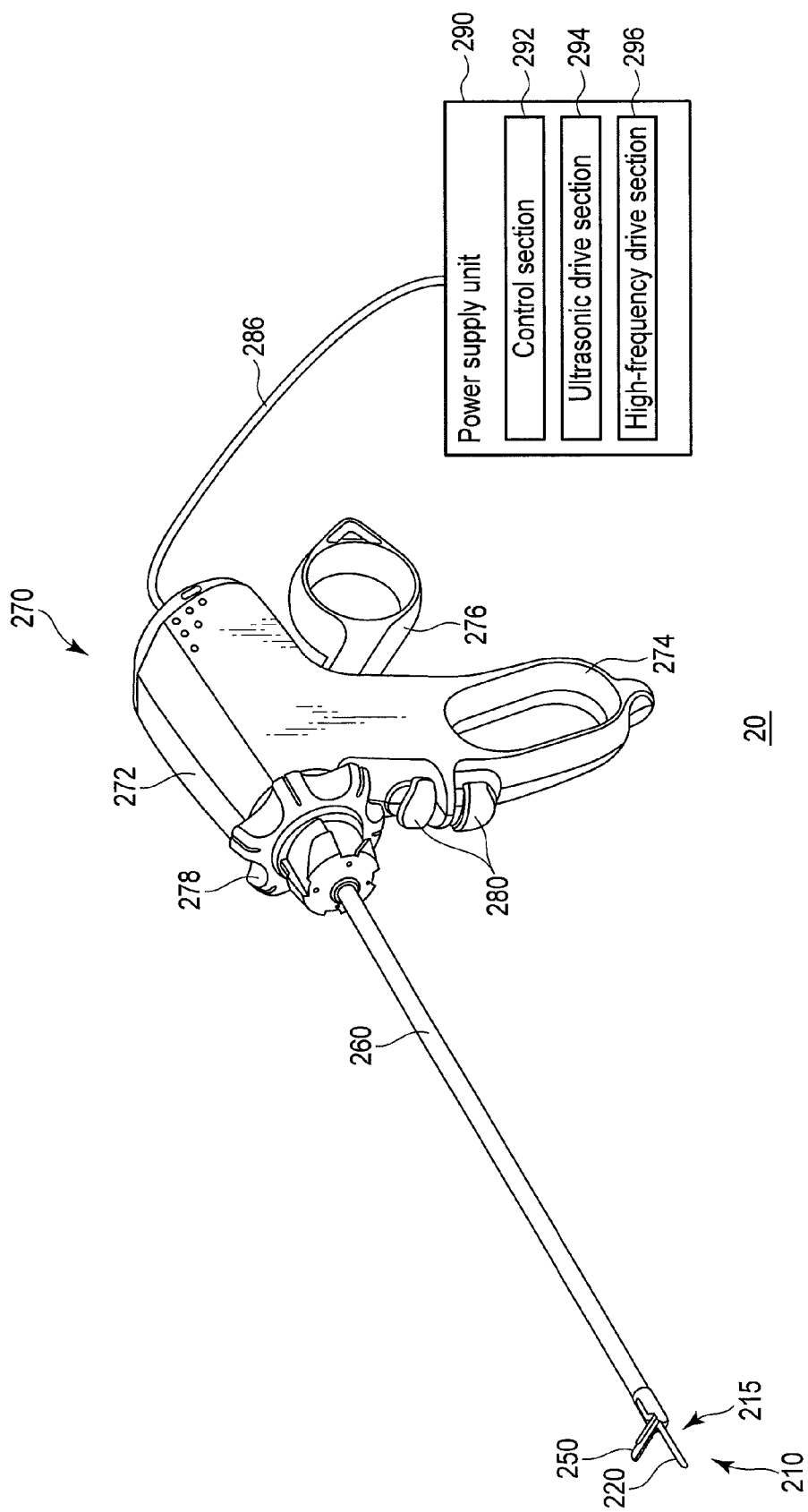
F I G. 9

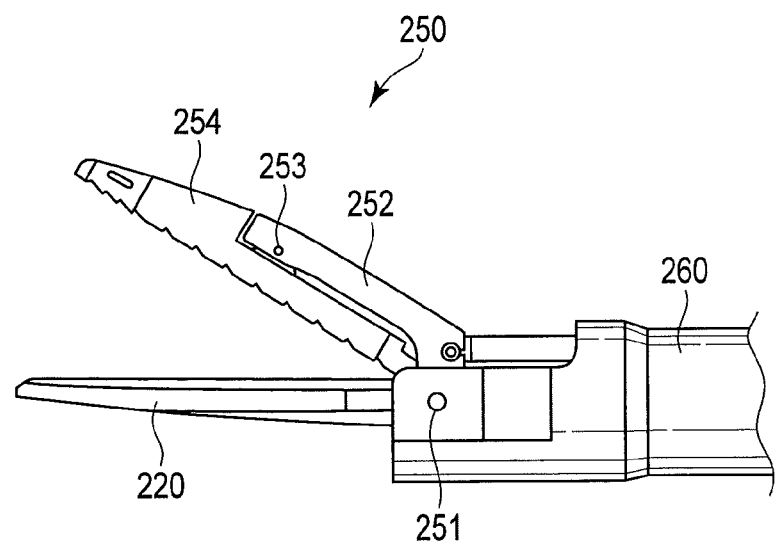
F I G. 12
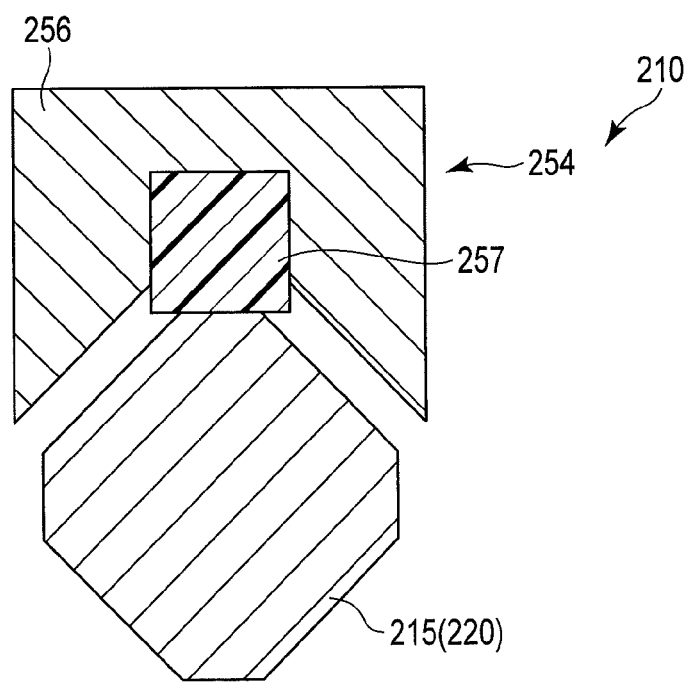
F I G. 13

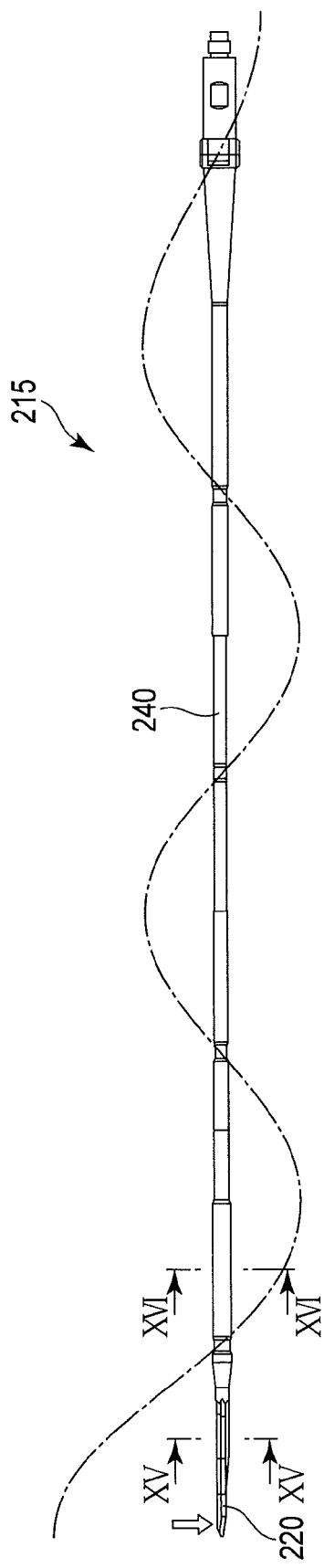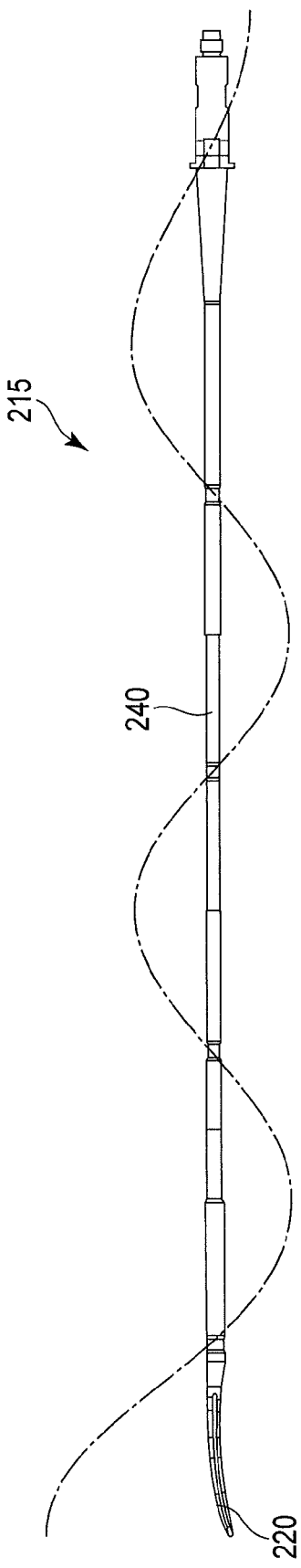
FIG. 14A
FIG. 14B

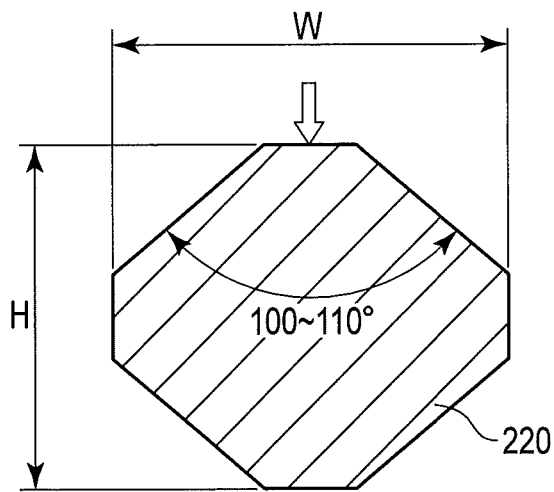
F I G. 15
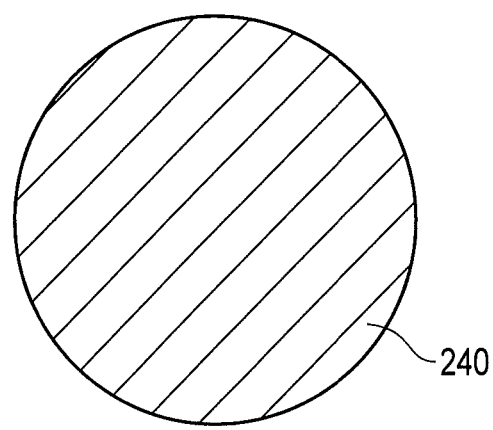
F I G. 16

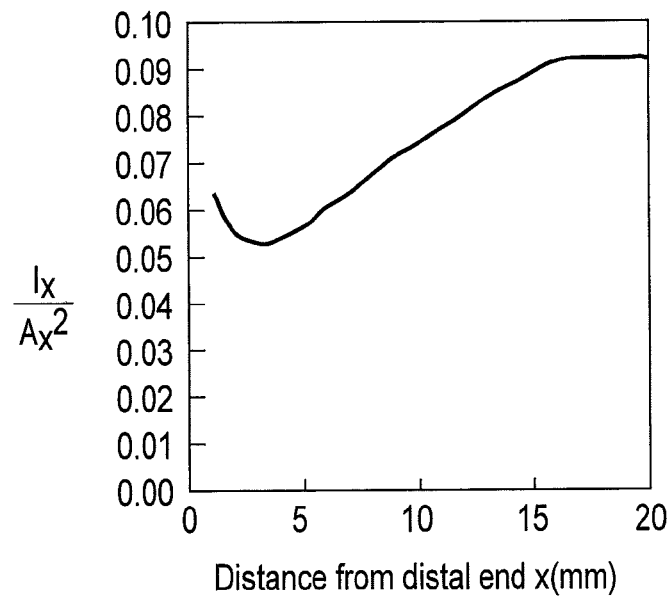
F I G. 18
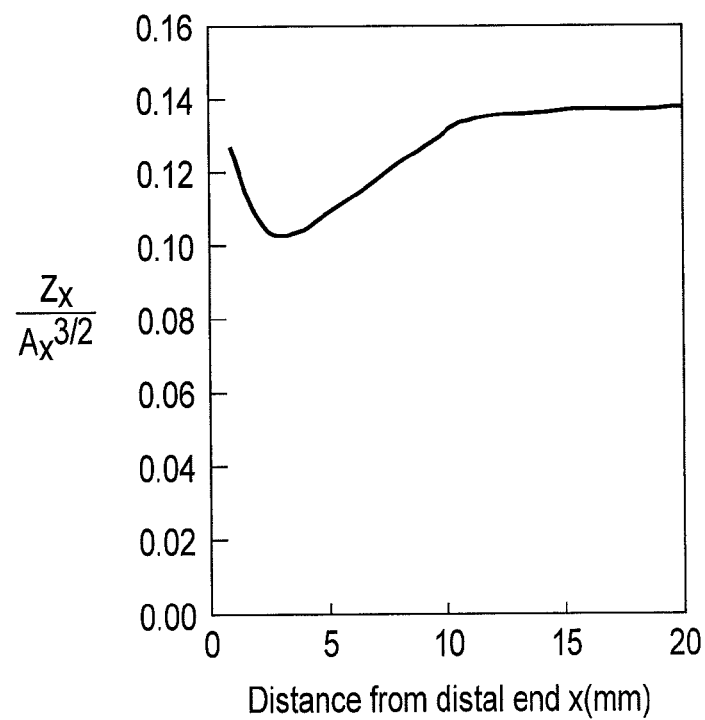
F I G. 19

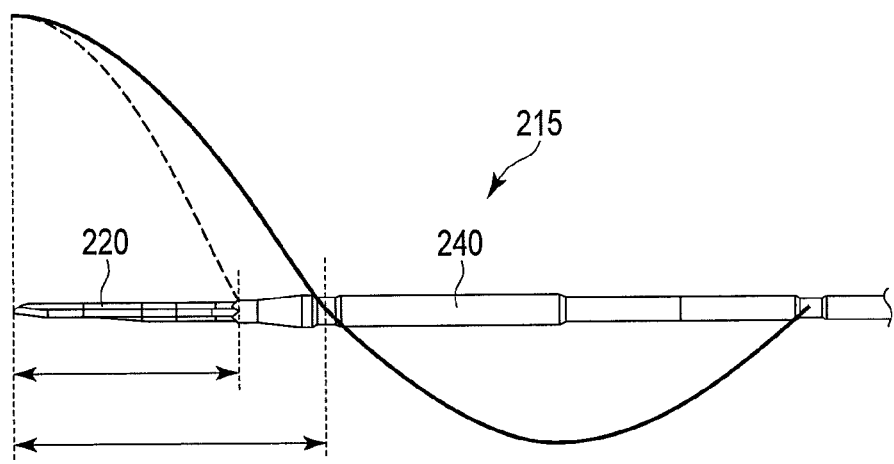
F I G. 20
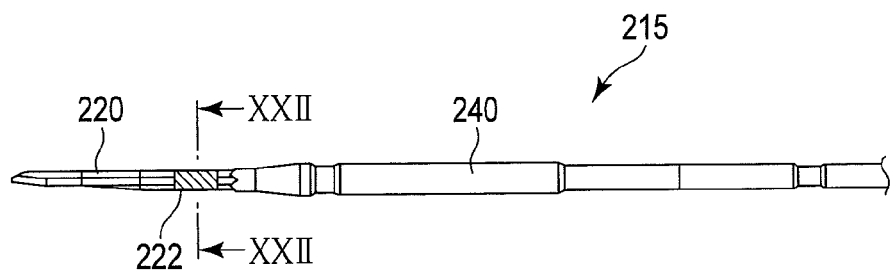
F I G. 21
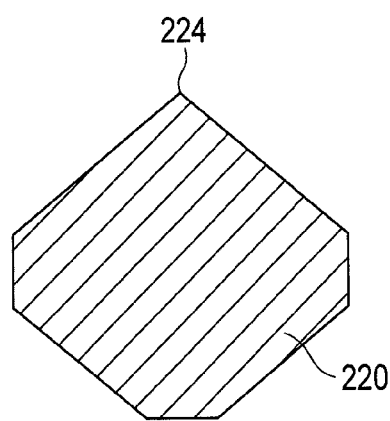
F I G. 22

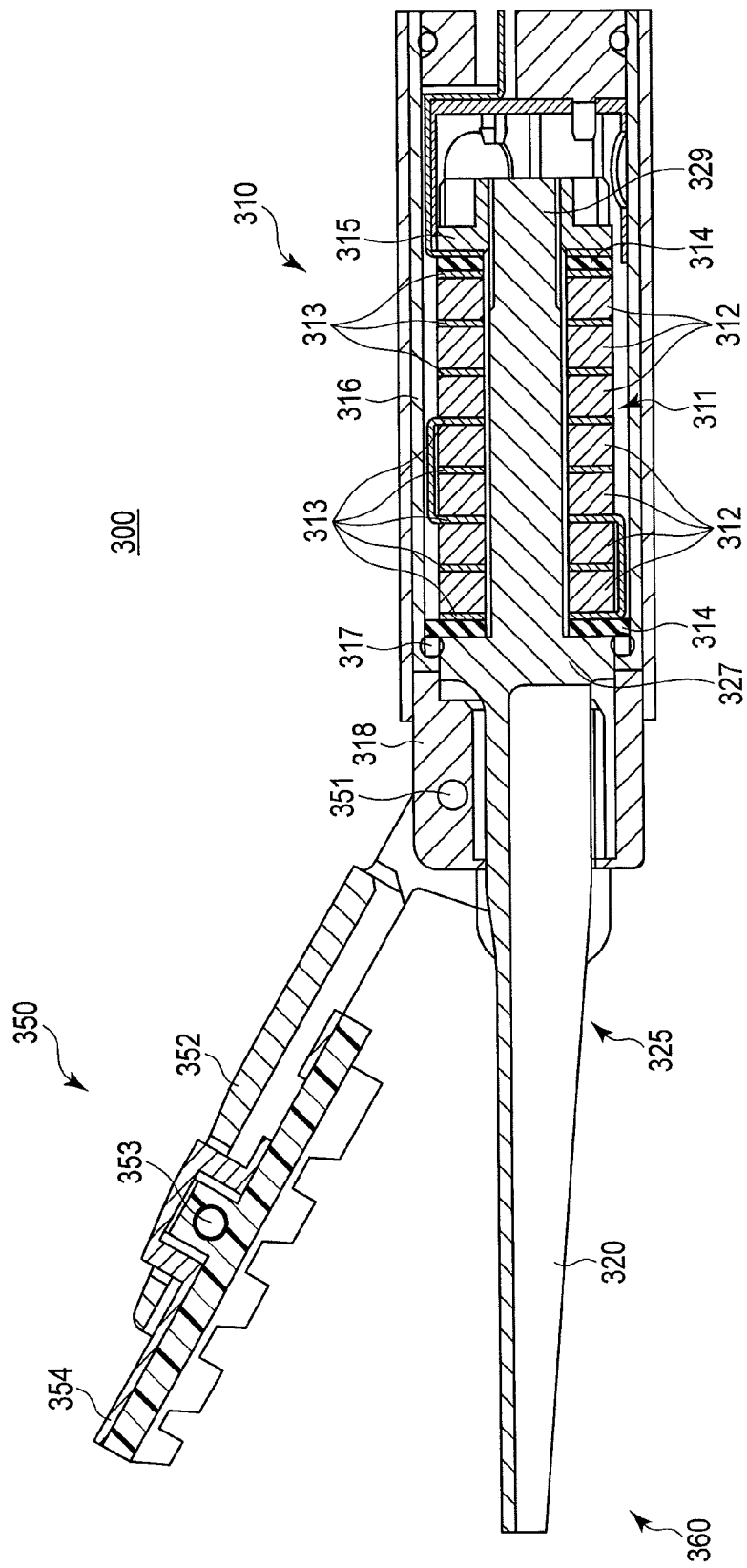
F I G. 23

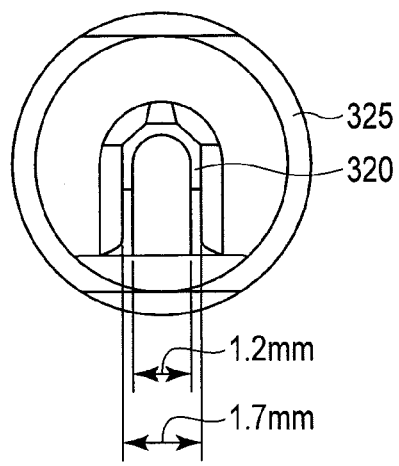
F I G. 27
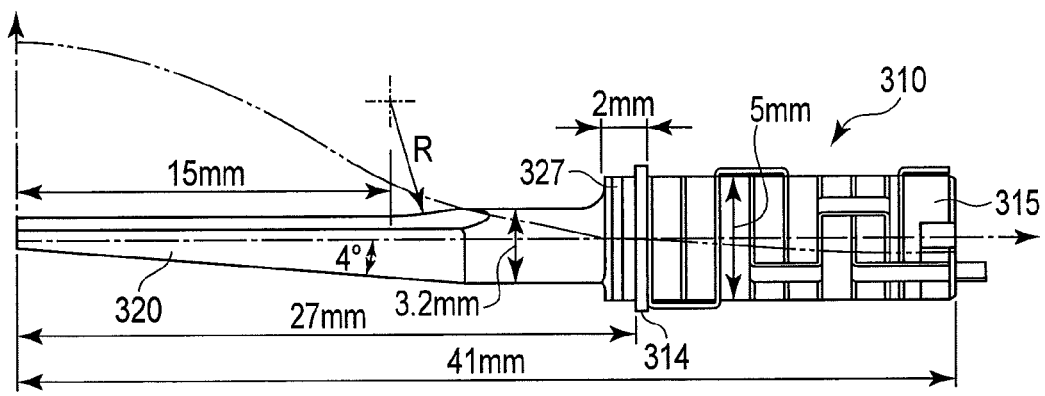
F I G. 28
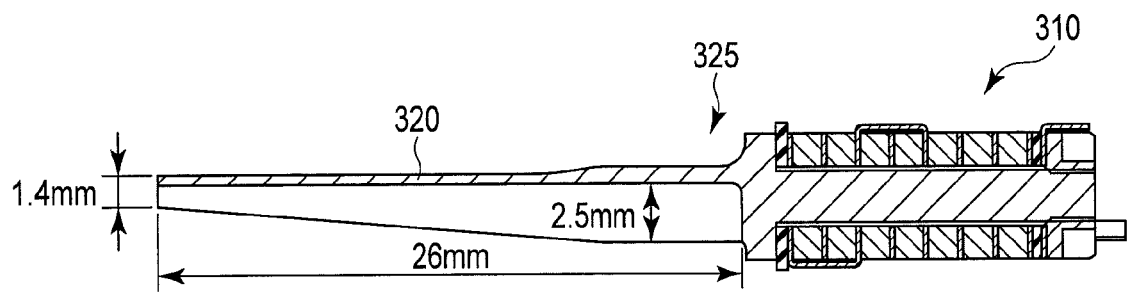
F I G. 29

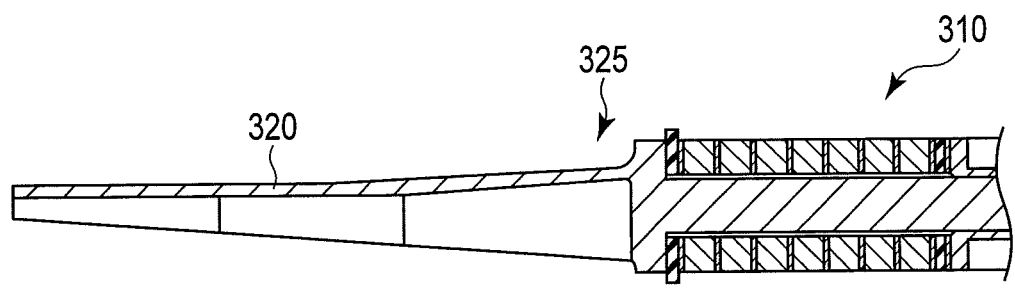
F I G. 32
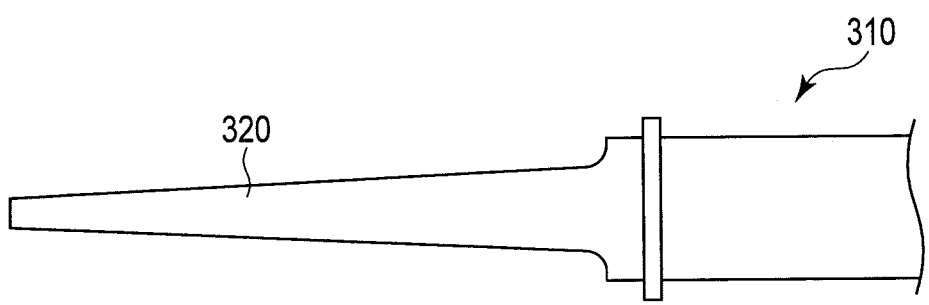
F I G. 33

TREATMENT DEVICE

CROSS-REFERENCE TO RELATED APPLICATIONS

This application is a Continuation Application of PCT Application No. PCT/JP2013/083168, filed Dec. 11, 2013 and based upon and claiming the benefit of priority from prior U.S. Provisional Application No. 61/736,806, filed Dec. 13, 2012, the entire contents of all of which are incorporated herein by reference.

BACKGROUND OF THE INVENTION

1. Field of the Invention

The present invention relates to a treatment device.

2. Description of the Related Art

There is known a forceps that grasps a biological tissue or the like as a treatment target in, for example, endoscopic surgery using a laparoscope. In endoscopic surgery, the forceps strongly grips a metallic clip on a grip section proximal end side in some situations. Moreover, at a proximal end of the grip section closer to a fulcrum point than at a distal end of the same, a gripping force increases more owing to a leverage ratio.

Further, there is also known an ultrasonic treatment device that grips a biological tissue by use of a grip member and a probe that transmits ultrasonic vibration and coagulates or incises the gripped biological tissue by ultrasonic vibration of the probe. For example, Jpn. Pat. Appln. KOKAI Publication No. 11-113922 discloses an example of such an ultrasonic treatment device. A velocity distribution of ultrasonic vibration in the probe is maximum at a distal end, and it is zero at a position corresponding to a ¼ wavelength from the distal end. A vibration velocity at a proximal end of the probe is smaller than a vibration velocity at a distal end of the probe. Therefore, a capability to coagulate or incise a biological tissue is poorer at the proximal end portion than at the distal end of the probe. Therefore, Jpn. Pat. Appln. KOKAI Publication No. 2005-288024 discloses a technique of increasing a gripping force at a proximal end portion of a probe to improve a capability to coagulate or incise a biological tissue at the proximal end portion of the probe. Furthermore, Jpn. Pat. Appln. KOKAI Publication No. 11-113922 discloses a technique of making a value of a section modulus of a probe at a proximal end portion higher than that at a distal end portion, to improve strength of the probe.

BRIEF SUMMARY OF THE INVENTION

According to an aspect of the invention, a treatment device includes: a first grip member having an elongated shape; and a second grip member which comprises a grip section that comes into contact with a biological tissue as a gripping target and which is displaced with respect to the first grip member to grip the biological tissue between the first grip member and the second grip member, wherein an end of the grip section on a side connected with the first grip member is a proximal end; an end of the grip section on a free end side is a distal end; and $I/A^2$ of the grip section is maximum at the proximal end, and/or $Z/A^{3/2}$ of the grip section is maximum at the proximal end, where I is a second moment of area, Z is a section modulus, and A is a cross-sectional area calculated based on an axis perpendicular to a straight line passing through a center of gravity of the first grip member and a center of gravity of the second grip member in a cross section perpendicular to a longitudinal axis of the grip section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a view showing an outline of a structural example of a distal end portion of the forceps according to the first embodiment;

FIG. 3 is a view showing an outline of a structural example of a first jaw according to the first embodiment;

FIG. 4 is a view showing the outline of the structural example of the first jaw according to the first embodiment;

FIG. 5 is a view showing the outline of the structural example of the first jaw according to the first embodiment;

FIG. 9 is a view showing an outline of a structural example of a treatment apparatus according to a second embodiment;

FIG. 12 is a view showing an outline of a structural example of a treatment section according to the second embodiment;

FIG. 13 is a view showing the outline of the structural example of the treatment section according to the second embodiment;

FIG. 14A is a view for explaining the outline of the structural example of the probe according to the second embodiment;

FIG. 14B is a view for explaining the outline of the structural example of the probe according to the second embodiment;

FIG. 15 is a view for explaining an outline of an example of a cross-sectional shape of a probe treatment section according to the second embodiment;

FIG. 16 is a view for explaining an outline of an example of a cross-sectional shape of a probe transmitting section according to the second embodiment;

FIG. 18 is a view showing an example of a relationship between a distance of the probe treatment section from the distal end and a value obtained by dividing a second moment of area by a square of a cross-sectional area according to the second embodiment;

FIG. 19 is a view showing a relationship between a distance of the probe treatment section from the distal end and a value obtained by dividing a section modulus by the 3/2 power of the cross-sectional area according to the second embodiment;

FIG. 20 is a view for explaining a modification of the probe treatment section according to the second embodiment;

FIG. 21 is a view for explaining the modification of the probe treatment section according to the second embodiment;

FIG. 22 is a view for explaining the modification of the probe treatment section according to the second embodiment;

FIG. 23 is a view showing an outline of a structural example of a treatment section according to a third embodiment;

FIG. 27 is a view showing an outline of a structural example of an ultrasonic transmission member according to the third embodiment;

FIG. 28 is a view showing the outline of the structural example of the ultrasonic transmission member according to the third embodiment;

FIG. 29 is a view showing the outline of the structural example of the ultrasonic transmission member according to the third embodiment;

FIG. 32 is a view showing a structural example of an ultrasonic transmission member according to a modification of the third embodiment; and FIG. 33 is a view showing a structural example of a probe treatment section according to the modification of the third embodiment.

DETAILED DESCRIPTION OF THE INVENTION

[First Embodiment]

A first embodiment according to the present invention will now be described with reference to the drawings.

Figure 1:
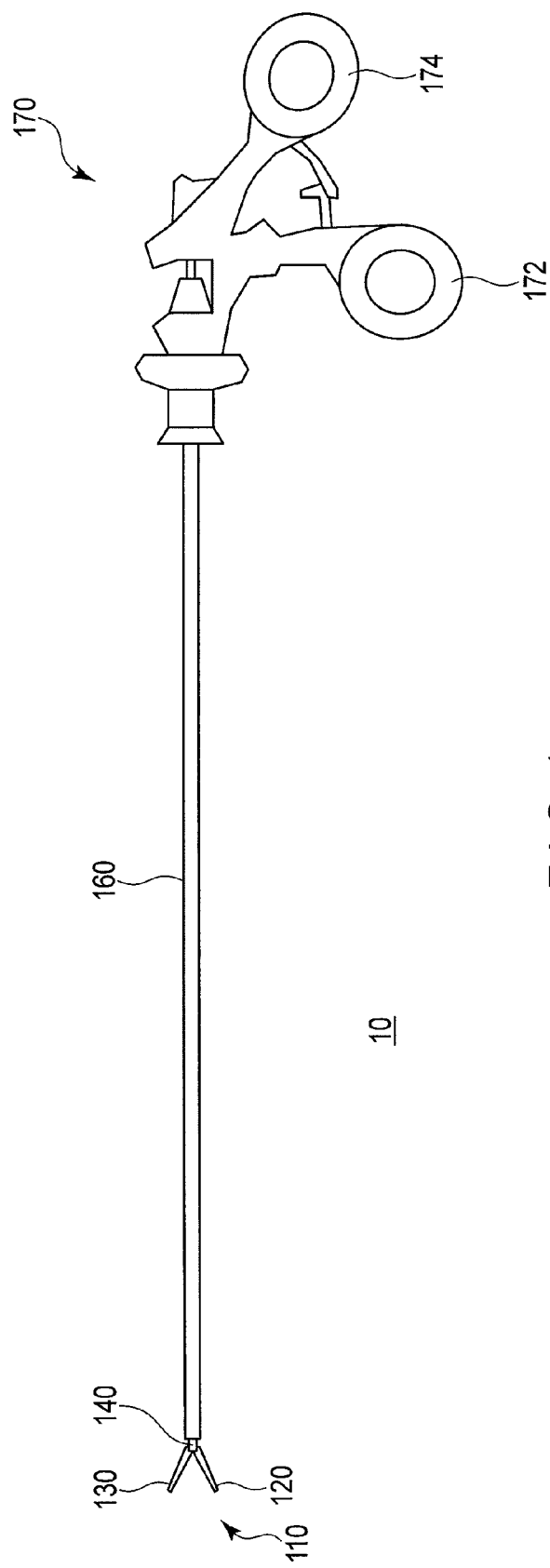
FIG. 1 is a view showing an outline of a structural example of a pair of forceps according to a first embodiment.

FIG. 1 shows a schematic view of a pair of forceps 10 according to this embodiment. As shown in this drawing, the forceps 10 includes a distal end portion 110, a shaft 160, and an operating section 170. The distal end portion 110 side will be referred to as a distal end side and the operating section 170 side will be referred to as a proximal end side hereinafter for illustrative purposes.

FIG. 2 shows a side elevation of the distal end portion 110. As shown in this drawing, the distal end portion 110 includes a first jaw 120 and a second jaw 130. The first jaw 120 and the second jaw 130 turn around a fulcrum pin 140 as an axis and perform an opening and closing operation. The distal end portion 110 grips a biological tissue by using the first jaw 120 and the second jaw 130.

The forceps 10 is used for, e.g., endoscopic surgery. The distal end portion 110 and the shaft 160 are inserted into, e.g., an abdominal cavity through a small hole formed in an abdominal wall of a subject. An operator manipulates the operating section 170 outside of the body of the subject to operate the distal end portion 110. Therefore, as shown in FIG. 1, the shaft 160 has an elongated shape.

The operating section 170 includes a fixed handle 172 and a movable handle 174. The movable handle 174 is displaced relative to the fixed handle 172. The movable handle 174 is connected with the first jaw 120 and the second jaw 130 of the distal end portion 110 through a wire or a rod inserted in the shaft 160, and the distal end portion 100 is opened or closed in accordance with an operation of the movable handle 174.

An operation of the forceps 10 according to this embodiment will now be described. An operator inserts the distal end portion 110 and the shaft 160 into an abdominal cavity through an abdominal wall. The operator moves the distal end portion 110 to be closer to a biological tissue as a treatment target. The operator operates the movable handle 174 to open or close the distal end portion 110 and grips the biological tissue as a gripping target by using the first jaw 120 and the second jaw 130. When the distal end portion 110 grips the biological tissue in this manner, a gripping load is applied to the first jaw 120 and the second jaw 130 of the distal end portion 110.

In this embodiment, the first jaw 120 and the second jaw 130 have the same shape. The shape of the first jaw 120 will now be described with reference to FIG. 3 to FIG. 5. FIG. 3 is a side elevation of the first jaw 120 as a component. A fulcrum hole 128 into which the fulcrum pin 140 is inserted and a working hole 129 into which a working pin on which force to be applied to the first jaw 120 is applied is inserted are provided in the first jaw 120. In the first jaw 120, a gripping surface 122 that comes into contact with a biological tissue is a flat surface. The first jaw 120 is tapered toward the distal end, and a height thereof is lowered toward the distal end. Therefore, a back side 124 that is a surface on the opposite side of the gripping surface 122 is inclined relative to the gripping surface 122. The height of the first jaw 120 is, e.g., 0.5 mm at the distal end and 2.5 mm at the proximal end.

FIG. 4 is a top view showing the first jaw 120 from the gripping surface 122 side. As shown in this drawing, a width of the first jaw 120 is also tapered toward the distal end. The width of the first jaw 120 is, e.g., 1 mm at the distal end and 3 mm at the proximal end. The first jaw 120 comes into contact with a biological tissue mainly through use of a gradually narrowed portion. This portion, the width of which gradually narrows, will be referred to as a grip section 125. A portion whose width is constant will be referred to as a proximal end portion 126. Further, a convex portion 127 is provided on the proximal end side of the proximal end portion 126. As shown in FIG. 4, a length of the grip section 125 is, e.g., 15 mm. Further, a length from the distal end including the grip section 125 and the proximal end portion 126 to the convex portion 127 is, e.g., 18 mm.

FIG. 5 is a front view showing the first jaw 120 from the distal end side. As shown in this drawing, a shape of a cross section of the first jaw 120 perpendicular to a longitudinal axis of the grip section 125 is rectangular at any position.

Figure 6:
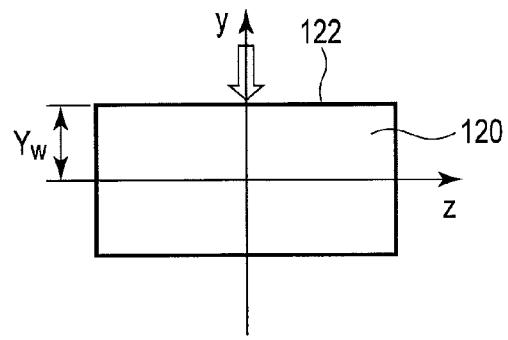
FIG. 6 is a view for explaining defined coordinate axes.

A second moment of area and a section modulus in the grip section 125 of the first jaw 120 will now be described. Consideration will now be given as to a cross section perpendicular to the longitudinal axis of the first jaw 120 when a distance from the distal end of the first jaw 120 is assumed to be x. As shown in FIG. 6, a coordinate system having a center of gravity of a cross section at the distance x from the distal end of the first jaw 120 as an origin will be considered. Here, as indicated by an open arrow in FIG. 6, it is assumed that a gripping load is perpendicularly applied to the gripping surface 122. A y axis is provided in a direction along which the gripping load is applied, and a z axis is provided in a direction perpendicular to the gripping load. At this time, a second moment of area $I_x$ calculated based on the z axis at the distance x from the distal end is provided by the following expression.

$$I_x = I_z(x) = \int_{A_x} y^2 dA_x$$

Here, $A_x$ is a cross-sectional area of the cross section at the distance x from the distal end.

Further, when a length Yw representing half of the height of the first jaw 120 is used, a section modulus $Z_x$ calculated based on the z axis at the distance x from the distal end is provided by the following expression.

$$Z_X = \frac{I_Z(x)}{Y_W}$$

Consideration will now be given as to a value $I_x/A_x^2$ obtained by dividing the second moment of area $I_x$ by a square of the cross-sectional area $A_x$ to make the second moment of area $I_x$ dimensionless. This value represents rigidity per unit area, i.e., difficulty in bending.

Figure 7:
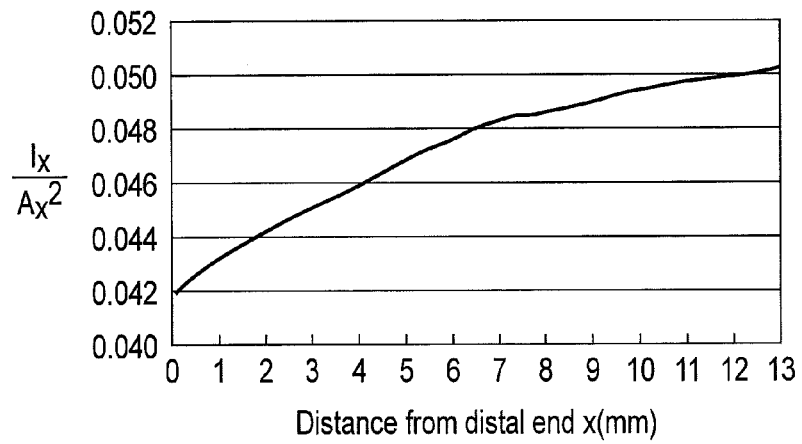
FIG. 7 is a view showing an example of a relationship between a distance from a distal end of the first jaw and a value obtained by dividing a second moment of area by a square of a cross-sectional area according to the first embodiment.

FIG. 7 shows a relationship between the distance x from the distal end and $I_x/A_x^2$ in the grip section 125 of the first jaw 120. As shown in this drawing, $I_x/A_x^2$ gradually increases from the distal end side toward the proximal end side. That is, the first jaw 120 according to this embodiment has higher rigidity per unit area on the proximal end side than on the distal end side.

Figure 8:
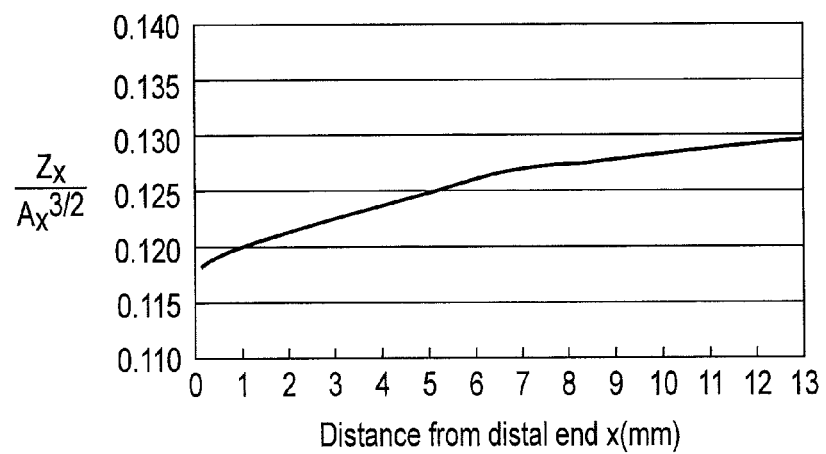
FIG. 8 is a view showing a relationship between a distance from the distal end of the first jaw and a value obtained by dividing the sectional modulus by the 3/2 power of a cross-sectional area according to the first embodiment.

Furthermore, consideration will now be given on a value $Z_x/A_x^{3/2}$ obtained by dividing the section modulus $Z_x$ by the 3/2 power of the cross-sectional area $A_x$ to make the section modulus $Z_x$ dimensionless. Since the section modulus $Z_x$ represents a value concerning stress on the gripping surface 122 on which maximum stress is applied, i.e., strength against bending, $Z_x/A_x^{3/2}$ represents difficulty in bending of the first jaw 120 per unit area. FIG. 8 shows a relationship between the distance x from the distal end and $Z_x/A_x^{3/2}$ in the grip section 125 of the first jaw 120. As shown in the drawing, $Z_x/A_x^{3/2}$ gradually increases from the distal end side toward the proximal end side. That is, the first jaw 120 according to this embodiment has higher strength against bending per unit area on the proximal end side than on the distal end side. Although $I_x/A_x^2$ and $Z_x/A_x^{3/2}$ of the first jaw 120 have been described here, they can be likewise applied to the second jaw 130.

In a laparoscopic forceps, a metallic clip is strongly gripped at the proximal end of the grip section 125 in some situations. A gripping force tends to increase more highly due to a leverage ratio on the proximal end side of the grip section 125 close to the fulcrum pin 140 than on the distal end side of the grip section 125. Therefore, for the grip section 125, higher strength is required on the proximal end side than on the distal end side. On the other hand, for the grip section 125, a thinner shape is desired because of easiness of a treatment, e.g., exfoliation. Moreover, when the grip section 125 bends, a treatment cannot be precisely performed, or visibility of peripheries of a treatment target lowers. Therefore, it is required for the grip section 125 not to bend.

Like the first jaw 120 and the second jaw 130 according to this embodiment, when design is performed in such a manner that the value $I_x/A_x^2$ obtained by dividing the second moment of area $I_x$ by a square of the cross-sectional area $A_x$ becomes larger on the proximal end side than on the distal end side, sufficient strength can be assured on the proximal end side where higher strength is required with respect to the first jaw 120 and the second jaw 130. Additionally, when design is performed in such a manner that the value $Z_x/A_x^{3/2}$ obtained by dividing the section modulus $Z_x$ by the 3/2 power of the cross-sectional area $A_x$ becomes larger on the proximal end side than on the distal end side, sufficient rigidity can be assured on the proximal end side where higher rigidity is required with respect to the first jaw 120 and the second jaw 130.

[Second Embodiment]

A second embodiment according to the present invention will now be described. Differences from the first embodiment alone will be explained here, and like reference numerals denote like parts to omit a description thereof. FIG. 9 shows a schematic view of a treatment apparatus 20 according to this embodiment. As shown in this drawing, the treatment apparatus 20 includes a treatment section 210, a shaft 260, an operating section 270, and a power supply unit 290. The distal end portion 210 side will be referred to as a distal end side and the operating section 270 side will be referred to as a proximal end side hereinafter for illustrative purposes. The treatment apparatus 20 grips a biological tissue as a treatment target, e.g., a blood vessel by using the treatment section 210, applies a high-frequency voltage to the gripped biological tissue, and seals or coagulates this biological tissue. Furthermore, the treatment apparatus 20 cuts the biological tissue gripped by the treatment unit 210 while performing, e.g., sealing by use of ultrasonic vibration.

The shaft 260 includes a hollow sheath. A probe 215 that transmits ultrasonic waves and vibrates in a longitudinal direction is arranged in this sheath. A proximal end of the probe 215 is placed in the operating section 270. A distal end side of the probe 215 constitutes a probe treatment section 220. The probe treatment section 220 protrudes from the sheath and is placed in the treatment section 210.

A jaw 250 is provided to the treatment section 210. The jaw 250 performs an opening and closing operation with respect to the distal end portion of the probe 215. Based on this opening and closing operation, the probe treatment section 220 and the jaw 250 grip a biological tissue as a treatment target. It is to be noted that part of the probe treatment section 220 and part of the jaw 250 function as a bipolar electrode that applies a high-frequency voltage to the gripped biological tissue. Part of the probe treatment section 220 or part of the jaw 250 may function as a monopolar electrode.

An operating section main body 272, a fixed handle 274, a movable handle 276, a rotation knob 278, and an output switch 280 are provided in the operating section 270. An ultrasonic vibrator unit is provided in the operating section main body 272. The proximal end side of the probe 215 is connected to this ultrasonic vibrator unit. An ultrasonic vibrator is provided in the ultrasonic vibrator unit, and ultrasonic vibration generated by the ultrasonic vibrator is transmitted through the probe 215. As a result, the probe treatment section 220 vibrates in the longitudinal direction, and the biological tissue gripped by the treatment section 210 is cut.

The fixed handle 274 is fixed to the operating section main body 272, and the movable handle 276 is displaced with respect to the operating section main body 272. The movable handle 276 is connected to a wire or a rod connected to the jaw 250 through the inside of the shaft 260. An operation of the movable handle 276 is transmitted to the jaw 250 via this wire or rod. The jaw 250 is displaced with respect to the probe treatment section 220 in accordance with an operation of the movable handle 276. The rotation knob 278 is a knob configured to rotate the distal end side of the rotation knob 278. The treatment section 210 and the shaft 260 rotate in accordance with rotation of the rotation knob 278, and an angle of the treatment section 210 is adjusted.

The output switch 280 includes, e.g., two buttons. When one button is pressed, the output switch 280 outputs a signal that enables the treatment section 210 to perform application of a high-frequency voltage and driving of the ultrasonic vibrator. As a result, the biological tissue gripped by the treatment section 210 is sealed, coagulated, or cut. Additionally, when the other button is pressed, the output switch 280 outputs a signal that enables application of the high-frequency voltage by the treatment section 210 but disables driving of the ultrasonic vibrator. As a result, the biological tissue gripped by the treatment section 210 is sealed or coagulated without being cut.

One end of a cable 286 is connected to the proximal end side of the operating section 270. The other end of the cable 286 is connected to the power supply unit 290. The power supply unit 290 includes a control section 292, an ultrasonic drive section 294, and a high-frequency drive section 296. The control section 292 controls the respective sections in the treatment apparatus 20. For example, the control section 292 controls operations of the ultrasonic drive section 294 or the high-frequency drive section 296 in accordance with an input from the output switch 280. The ultrasonic drive section 294 drives the ultrasonic vibrator under control of the control section 292. The high-frequency drive section 296 supplies a high-frequency current to the treatment section 210 under control of the control section 292.

An operation of the treatment apparatus 20 according to this embodiment will now be described. An operator operates an input section of the power supply unit 290 to set output conditions of the treatment apparatus, e.g., set the electric power to high-frequency energy output, ultrasonic energy output, or other output. The treatment apparatus 20 may be configured so that each value can be individually set or a set of set values corresponding to an operative procedure can be selected.

The treatment section 210 and the shaft 260 are inserted into, e.g., an abdominal cavity through an abdominal wall. The operator operates the movable handle 276 to open or close the treatment section 210, and a biological tissue as a treatment target is gripped by the probe treatment section 220 and the jaw 250. After gripping the biological tissue by using the treatment section 210, the operator operates the output switch 280. When one of two buttons in the output switch 280 is pressed, the output switch 280 outputs a signal that enables the treatment section 210 to perform application of a high-frequency voltage and driving of the ultrasonic vibrator. The control section 292 of the power supply unit 290 that has acquired this signal outputs an instruction concerning driving to the ultrasonic drive section 294 and the high-frequency drive section 296.

The high-frequency drive section 296 applies a high-frequency voltage to the probe treatment section 220 and the jaw 250 in the treatment section 210 under control of the control section 292 and allows a high-frequency current to flow through the biological tissue as the treatment target. When the high-frequency current flows, since the biological tissue has electrical resistance, heat is generated in the biological tissue, and a temperature of the biological tissue increases. The temperature of the biological tissue at this moment is, e.g., approximately 100° C. As a result, protein denatures, and the biological tissue is coagulated and sealed.

Then, the ultrasonic drive section 294 drives the ultrasonic vibrator under control of the control section 292. As a result, the probe treatment section 220 vibrates in the longitudinal direction thereof at an ultrasonic frequency. A temperature of the biological tissue increases by friction heat of the biological tissue and the probe treatment section 220. As a result, the protein denatures, and the biological tissue is coagulated and sealed. It is to be noted that this biological tissue sealing effect based on the ultrasonic vibration is weaker than the sealing effect based on application of a high-frequency voltage. Further, a temperature of the biological tissue is, e.g., approximately 200° C. As a result, the biological tissue collapses, and the biological tissue is cut. In this manner, the biological tissue gripped by the treatment section 210 is coagulated and cut while being sealed. Then, the treatment for the biological tissue is completed.

Figure 10:
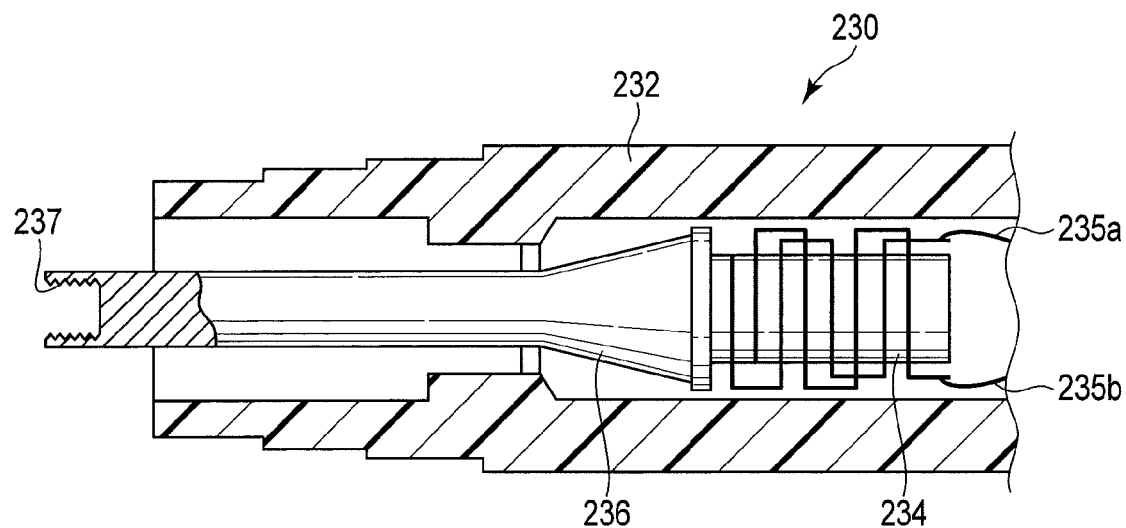
FIG. 10 is a view showing an outline of a structural example of a probe according to the second embodiment.

A vibrator unit 230 in the operating section main body 272 will now be described with reference to FIG. 10. As shown in this drawing, the vibrator unit 230 has a vibrator case 232. An ultrasonic vibrator 234 that generates ultrasonic vibration by an inverse piezoelectric effect is provided in the vibrator case 232. An electric signal wire 235a and electric signal wire 235b as a pair are connected to the ultrasonic vibrator 234. The ultrasonic vibrator 234 is connected to the ultrasonic drive section 294 in the power supply unit 290 through the electric signal wire 235a and the electric signal wire 235b, and the cable 286. The ultrasonic vibrator 234 is driven by the ultrasonic drive section 294 to produce the ultrasonic vibration. A columnar horn 236 is coupled with the distal end side of the ultrasonic vibrator 234 to enlarge an amplitude of the ultrasonic vibration. The horn 236 is supported by the vibrator case 232. A female screw 237 is formed at a distal end portion of the horn 236.

Figure 11:
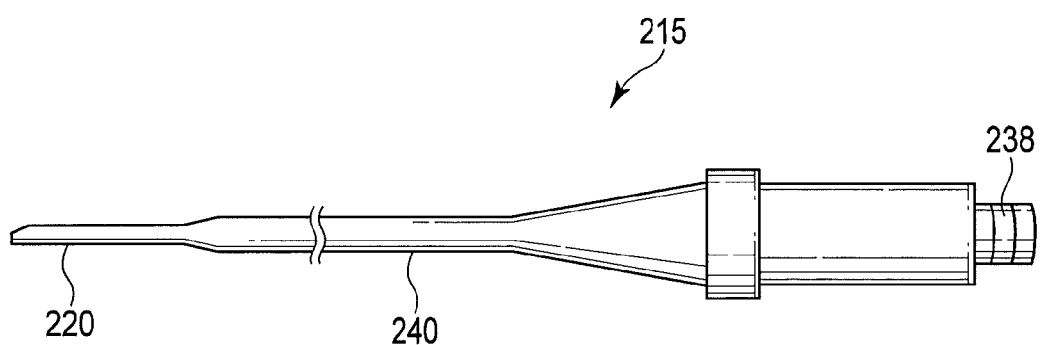
FIG. 11 is a view showing the outline of the structural example of the probe according to the second embodiment.

FIG. 11 shows a configuration of the probe 215. As shown in this drawing, a male screw 238 is provided at a proximal end portion of the probe 215. The male screw 238 of the probe 215 is disposed to the female screw 237 of the horn 236. When the probe 215 is disposed to the horn 236, the ultrasonic vibration generated by the ultrasonic vibrator 234 is transmitted to the probe treatment section 220 at the distal end of the probe 215. In this manner, the probe 215 transmits the ultrasonic vibration from the proximal end to the distal end. A portion of the probe 215 on the proximal end side of the probe treatment section 220 will be referred to as a probe transmitting section 240.

FIG. 12 shows a side elevation of the treatment section 210. The probe treatment section 220 that is a distal end portion of the probe 215 protrudes from the distal end of the shaft 260. A support member 252 of the jaw 250 is provided at the distal end portion of the shaft 260 to be rotatable around a first rotary shaft 251 as a center axis. A second rotary shaft 253 is provided near a distal end of the support member 252, and a grip member 254 is provided to be rotatable around the second rotary shaft 253 as a center axis. The grip member 254 can rotate with respect to the support member 252 in accordance with a position of the support member 252. As a result, even if a thickness of the biological tissue to be gripped differs between the distal end side and the proximal end side, the biological tissue can be gripped with a pressure that is equal on both the distal end side and the proximal end side. Applying a uniform pressure to the biological tissue as a treatment target brings about stable sealing, coagulation, and incision of the biological tissue. A length of the probe treatment section 220, i.e., a length of a portion of the probe 215 that faces the jaw 250 is approximately 20 mm.

FIG. 13 shows a cross-sectional view of the treatment section 210 in a cross section perpendicular to the longitudinal axis of the probe 215. In this drawing, the probe 215 and the grip member 254 of the jaw 250 are closed. As shown in this drawing, the probe 215 in the treatment section 210, i.e., the probe treatment section 220 has an octagonal cross-sectional shape. Further, the grip member 254 has an electrode section 256 and a pad member 257. The pad member 257 is made of an insulating material such as a fluororesin. In a state that the treatment section 210 is closed, the probe treatment section 220 and the pad member 257 contact each other, and a gap is formed between the probe treatment section 220 and the electrode section 256. At the time of using the treatment apparatus 20, when the treatment section 210 grips the biological tissue and a high-frequency voltage is applied, a current flows through the biological tissue placed in this gap portion. As a result, the biological tissue in a portion through which the current has flowed is sealed or coagulated. Furthermore, when the ultrasonic vibrator 234 vibrates, the probe treatment section 220 moves in the longitudinal axis direction thereof, and the biological tissue is rubbed against the probe treatment section 220 and cut in a portion sandwiched between the pad member 257 and the probe treatment section 220.

FIG. 14A shows a side elevation of the probe 215, and FIG. 14B shows a top view of the probe 215. In these drawings, a dashed-dotted line represents a vibration velocity distribution when the probe 215 vibrates. Moreover, an open arrow in FIG. 14A represents a direction along which a gripping load is applied when the biological tissue is gripped. As shown in FIG. 14B, the distal end side of the probe treatment section 220 is curved in a gripping surface that grips the biological tissue. A total length of the probe 215 is, e.g., 240 mm, and a length of the probe treatment section 220 facing the jaw 250 is approximately 20 mm.

A vibration frequency of the ultrasonic wave transmitted by the probe 215 is, e.g., 47 kHz, and a wavelength is, e.g., 95 mm. That is, as shown in FIG. 14A and FIG. 14B, the length of the probe 215 is set to a length corresponding to 2.5 wavelengths. Additionally, the length of the probe treatment section 220 is set to approximately 0.8 times of a quarter wavelength.

A maximum outer diameter of the probe transmitting section 240 is, e.g., 3.5 mm. An outer diameter of the shaft 260 is, e.g., 8 mm. Since the distal end portion of the probe 215 is narrower than the proximal end portion of the same, the vibration velocity is increased on the distal end portion side. The vibration velocity in the probe 215 is, e.g., 3 m/sp-p in the proximal end portion, and it is, e.g., 24 m/sp-p in the distal end portion.

FIG. 15 shows a cross-sectional shape of the probe 215 along a line XV-XV line depicted in FIG. 14A, namely, in the probe treatment section 220. As shown in the drawing, a cross-sectional shape of the probe treatment section 220 on the proximal end side is an octagon. Here, in FIG. 15, a surface indicated by an open arrow is a surface facing the jaw 250. An angle formed by two sides adjacent to a side facing this jaw 250 is, e.g., 100 to 110°. Assuming that a length of the probe treatment section 220 in a direction along which a gripping load is applied is a height H and a length in a direction perpendicular to the height direction is a width W, a ratio of the width W and the height H is, e.g., W:H=1 to 1.2:1. It is to be noted that FIG. 16 shows a cross-sectional shape of the probe 215 along a line XVI-XVI depicted in FIG. 14A, namely, in the probe transmitting section 240. As shown in this drawing, the cross-sectional shape of the probe transmitting section 240 is a circle.

Figure 17A:
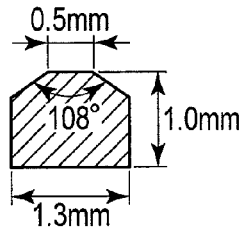
FIG. 17A is a view for explaining an outline of an example of a cross-sectional shape of the probe treatment section at a position that is 1 mm from a distal end according to the second embodiment.
Figure 17B:
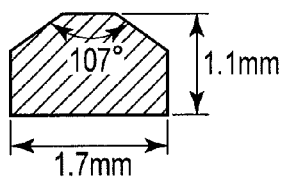
FIG. 17B is a view for explaining an outline of an example of a cross-sectional shape of the probe treatment section at a position that is 2 mm from the distal end according to the second embodiment.
Figure 17C:
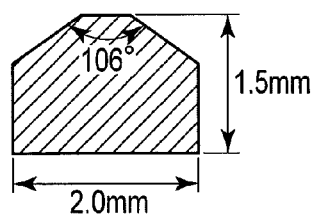
FIG. 17C is a view for explaining an outline of an example of a cross-sectional shape of the probe treatment section at a position that is 6 mm from the distal end according to the second embodiment.
Figure 17D:
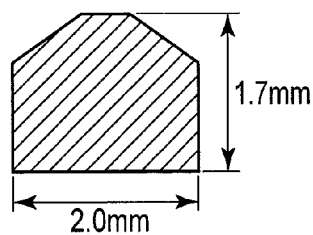
FIG. 17D is a view for explaining an outline of an example of a cross-sectional shape of the probe treatment section at a position that is 9 mm from the distal end according to the second embodiment.
Figure 17E:
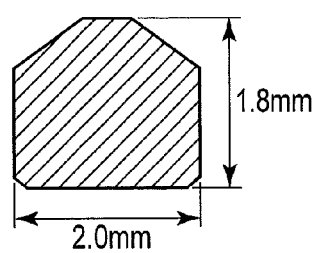
FIG. 17E is a view for explaining an outline of an example of a cross-sectional shape of the probe treatment section at a position that is 11 mm from the distal end according to the second embodiment.
Figure 17F:
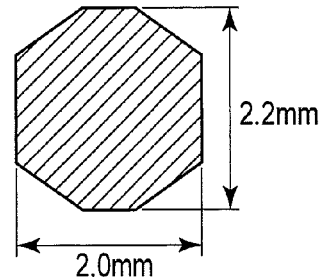
FIG. 17F is a view for explaining an outline of an example of a cross-sectional shape of the probe treatment section at a position that is 15 mm from the distal end according to the second embodiment.
Figure 17G:
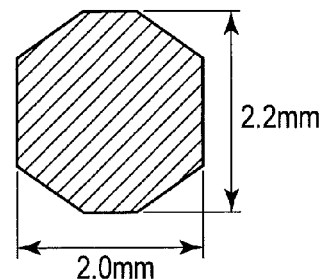
FIG. 17G is a view for explaining an outline of an example of a cross-sectional shape of the probe treatment section at a position that is 18 mm from the distal end according to the second embodiment.
Figure 17H:
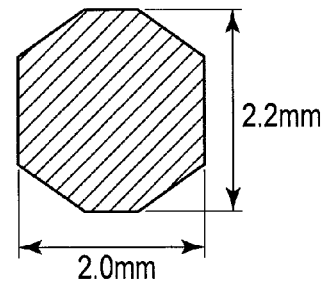
FIG. 17H is a view for explaining an outline of an example of a cross-sectional shape of the probe treatment section at a position that is 20 mm from the distal end according to the second embodiment.
Figure 17I:
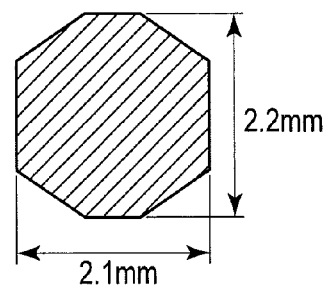
FIG. 17I is a view for explaining an outline of an example of a cross-sectional shape of the probe treatment section at a position that is 21 mm from the distal end according to the second embodiment.

The back side of the probe treatment section 220 present on the opposite side of the gripping surface is cut and narrowed toward the distal end, and hence the cross-sectional shape of the probe treatment section 220 differs depending on a position from the distal end. Each of FIG. 17A to FIG. 17i shows the cross-sectional shape of the probe treatment section 220 according to this embodiment at a distance x from the distal end. Here, FIG. 17A shows a cross section at a position that is 1 mm from the distal end; FIG. 17B, 2 mm from the distal end; FIG. 17C, 6 mm from the distal end; FIG. 17D, 9 mm from the distal end; FIG. 17E, 11 mm from the distal end; FIG. 17F, 15 mm from the distal end; FIG. 17G, 18 mm from the distal end; FIG. 17H, 20 mm from the distal end; and FIG. 17I, 21 mm from the distal end, respectively. As shown in the drawings, the probe treatment section 220 according to this embodiment has a shape obtained by cutting off the octagonal column described with reference to FIG. 15 from the back side provided on the opposite side of the gripping surface. Further, a portion that is 3 mm or less from the distal end has a width narrower than other portions.

As in the description of the first embodiment, FIG. 18 shows a relationship between a distance x from the distal end and a value obtained by dividing a second moment of area $I_x$ by a square of a cross-sectional area $A_x$ in the probe treatment section 220, i.e., $I_x/A_x^2$. As shown in this drawing, $I_x/A_x^2$ gradually decreases from the distal end side toward the proximal end side up to a position that is approximately 3 mm from the distal end, but $I_x/A_x^2$ gradually increases from the distal end side toward the proximal end side on the proximal end side of the position that is approximately 3 mm from the distal end. Further, at the most proximal position, $I_x/A_x^2$ becomes maximum. That is, the probe treatment section 220 according to this embodiment has rigidity per unit area that gradually increases from the distal end side toward the proximal end side and becomes maximum at the proximal end on the proximal end side of the position that is approximately 3 mm from the distal end.

Furthermore, FIG. 19 shows a relationship between the distance x from the distal end and a value obtained by dividing a section modulus $Z_x$ by the 3/2 power of the cross-sectional area $A_x$ in the probe treatment section 220, i.e., $Z_x/A_x^{3/2}$. As shown in this drawing, $Z_x/A_x^{3/2}$ gradually decreases from the distal end side toward the proximal end side up to the position that is approximately 3 mm from the distal end, but $Z_x/A_x^{3/2}$ gradually increases from the distal end side toward the proximal end side on the proximal end side of the position that is approximately 3 mm from the distal end. Moreover, $Z_x/A_x^{3/2}$ becomes maximum at the most proximal position. That is, in the probe treatment section 220 according to this embodiment, strength against bending per unit area is gradually increased from the distal end side toward the proximal end side, and the strength against to bending per unit area becomes maximum at the proximal end on the proximal end side of the position that is approximately 3 mm from the distal end.

As indicated by a dashed-dotted line in FIG. 14A, the ultrasonic vibration velocity in the probe 215 becomes maximum at the distal end of the probe treatment section 220 and becomes zero at a position where the distance from the distal end is equal to the length corresponding to a quarter wavelength. That is, the vibration velocity of the probe treatment section 220 is lower on the proximal end side than on the distal end side. Therefore, incision of the biological tissue using the ultrasonic vibration in the treatment section 210 is more difficult on the proximal end side than on the distal end. It is desirable that the gripping force of the probe treatment section 220 and the jaw 250 increases more on the proximal end side than on the distal end side so that an uncut portion of the biological tissue is not produced on the proximal end side of the treatment section 210. If the gripping force is increased on the proximal end side, the probe treatment section 220 must be resistant to bending and have high strength on the proximal end side. On the other hand, to increase the vibration velocity of the ultrasonic vibration, the probe treatment section 220 must be thin. If the vibration velocity of the probe treatment section 220 is too high, a temperature of the biological tissue is not sufficiently increased, coagulation is not satisfactorily performed, and incision alone is carried out. Therefore, cross-sectional areas of the probe treatment section 220 on the distal end side and the proximal end side must have appropriate values.

When the probe treatment section 220 is formed into the shape as in this embodiment, $I_x/A_x^2$ is larger on the proximal end side than on the distal end side while maintaining appropriate cross-sectional areas, so that it is more difficult to bend on the proximal end side than on the distal end side. Further, as in this embodiment, $Z_x/A_x^{3/2}$ is larger on the proximal end side than on the distal end side, so that the strength is higher on the proximal end side than on the distal end side. That is, according to this embodiment, sufficient difficulty in bending and the sufficient strength can be assured while maintaining appropriate cross-sectional areas.

It is to be noted that, to improve the coagulation/incision capability at the proximal end of the treatment section 210, for example, the following ingenuity can be adopted in addition to this embodiment.

When the thickness of the probe 215 is changed in accordance with the distal end side and the proximal end side, a wavelength of the ultrasonic wave to be transmitted can be varied. That is, for example, such a velocity distribution as indicated by a broken line in FIG. 20 can be provided if the proximal end and the distal end of the probe 215 have the same diameter, but such a velocity distribution as indicated by a solid line in FIG. 20 can be provided if the proximal end side has a larger thickness than the distal end side. This can be represented by the following Expressions. If the proximal end and the distal end have the same diameter, a wavelength λ is provided by the following expression based on a resonance frequency f and sonic velocity c.

$$\lambda = \frac{c}{2f}$$

On the other hand, if the proximal end is thick whilst the distal end is thin and both the proximal end and the distal end are formed by using exponential curves, the wavelength λ is provided by the following expression.

$$\lambda = \frac{c}{2f}\sqrt{1+\left(\frac{1}{2\pi}\ln\frac{S_2}{S_1}\right)^2}$$

Here, $S_1$ represents a cross-sectional area of the proximal end, and $S_2$ represents a cross-sectional area of the distal end. When the thickness of the probe 215 is adjusted in this manner, the vibration velocity distribution including a position of a node can be adjusted.

Furthermore, in a case where the probe treatment section 220 is provided with residual stress, heat is generated at a position where this residual stress is provided when the probe treatment section 220 is subjected to the ultrasonic vibration. This heat enables the treatment section 210 to have an improved capability of incising the biological tissue or an improved capability of coagulating the biological tissue in a portion provided with the residual stress. To improve the treatment capability on the proximal end side of the treatment section 210, for example, it is also effective to provide residual stress to a portion shaded as a proximal end portion 222 in FIG. 21.

Moreover, besides the residual stress, when a metal having a higher specific gravity than those of other portions is used, heat is generated in such metal portion. Therefore, in the probe treatment section 220 made of, e.g., a titanium alloy, when a metal having a higher specific gravity than a titanium alloy, e.g., a stainless steel is used for the portion shaded as the proximal end portion 222 in FIG. 21, the treatment capability of the treatment section 210 on the proximal end side can be increased.

Additionally, to improve the incision capability in the proximal end portion 222 of the treatment section 210, a cross-sectional shape of the proximal end portion 222 can be formed as shown in, e.g., FIG. 22. That is, the surface of the probe treatment section 220 facing the jaw 250 can be formed into a shape provided with an edge 224 without being formed into a flat surface.

[Third Embodiment]

A third embodiment according to the present invention will now be described. Here, a difference from the second embodiment will be described, and like reference numerals denote like parts to omit a description thereof. In the second embodiment, the ultrasonic vibrator 234 is provided to the operating section 270, and the ultrasonic wave is transmitted to the probe treatment section 220 of the treatment section 210 by the probe 215 inserted in the shaft 260. On the other hand, in this embodiment, an ultrasonic vibrator is provided at a distal end of a shaft 260.

FIG. 23 shows a structural example of a treatment section 300 provided at the distal end portion of the shaft 260 according to this embodiment. It is to be noted that, in this embodiment, since the ultrasonic vibrator is provided at the distal end portion of the shaft 260, the ultrasonic vibrator is not provided in the operating section 270, and a probe transmitting section 240 that transmits the ultrasonic wave is not provided in the shaft 260. A configuration of a treatment apparatus 20 is the same as that in the second embodiment described with reference to FIG. 9 except in these aspects.

As shown in FIG. 23, the treatment section 300 includes an ultrasonic vibrator 310, a probe treatment section 320, and a jaw 350. Seven piezoelectric elements 312 are included in the ultrasonic vibrator 310. These piezoelectric elements 312 have an annular shape, and they are laminated so that each element is sandwiched between respective electrodes 313 having an annular shape. Annular-shaped insulating plates 314 are provided at both ends of the ultrasonic vibrator 310. When the piezoelectric elements 312, the electrodes 313, and the insulating plates 314 each having the annular shape are laminated in this manner, a hollow vibration member 311 having a cylindrical shape as a whole is configured.

An ultrasonic transmission member 325 is provided to the treatment section 300. A distal end side of the ultrasonic transmission member 325 constitutes a probe treatment section 320. A convex portion 327 is provided at a proximal end of the probe treatment section 320 of the ultrasonic transmission member 325. A vibration member 311 including the piezoelectric elements 312 and others is appressed against this convex portion 327. A piercing portion 329 is provided on the proximal end side of the convex portion 327 of the ultrasonic transmission member 325. The piercing portion 329 pierces through a central portion of the cylindrical vibration member 311. That is, the piercing portion 329 pierces through the piezoelectric elements 312, the electrodes 313, the insulating plates 314, and others. The piercing portion 329 is in contact with the piezoelectric elements 312 and the insulating plates 314 but not in contact with the electrodes 313. A lining plate 315 is provided on the proximal end side of the piercing portion 329. The lining plate 315 presses the ultrasonic vibrator 310 against the convex portion 327 of the ultrasonic transmission member 325.

The vibration member 311 is arranged in a cylinder 316. This cylinder 316 serves as a cover that covers the ultrasonic vibrator 310. An O-ring 317 is provided at an end portion of the cylinder 316 on the distal end side. The O-ring 317 seals a gap between the ultrasonic transmission member 325 and the cylinder 316 to prevent a liquid from entering the inside of the cylinder 316. A coupling member 318 is provided on the distal end side of the cylinder 316. The jaw 350 is connected to the coupling member 318. The probe treatment section 320 and the jaw 350 constitute a treatment section 360. A support member 352 of the jaw 350 is provided to the coupling member 318 to be rotatable around a first rotary shaft 351 as a center axis provided to the coupling member 318.

A second rotary shaft 353 is provided near a distal end of the support member 352, and a grip member 354 is provided to be rotatable around the second rotary shaft 353 as a center axis. The grip member 354 can rotate with respect to the support member 352 in accordance with a position of the support member 352. As a result, even if a thickness of a gripped biological tissue differs between the distal end side and the proximal end side, the treatment section 360 can grip the biological tissue with a pressure that is the same on the distal end side and the proximal end side. Applying uniform pressure to the biological tissue as a treatment target brings about stable sealing, coagulation, and incision of the biological tissue.

Figure 24:
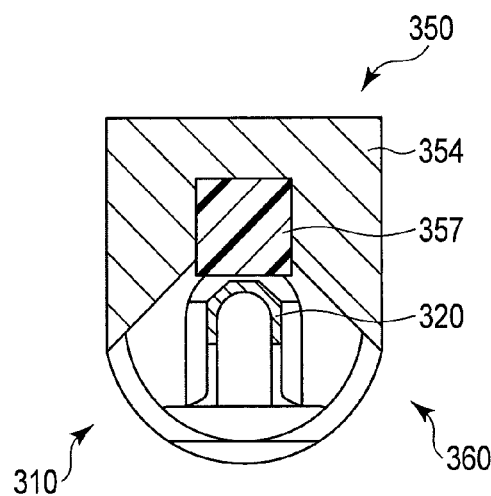
FIG. 24 is a view showing an outline of a structural example of a distal end treatment section according to the third embodiment.

FIG. 24 shows a cross-sectional view of the probe treatment section 320 and the grip member 354 as seen from the distal end side in a state that the treatment section 360 is closed. As shown in this drawing, when a surface of the probe treatment section 320 facing the grip member 354 is determined as a gripping surface, a groove is provided in a surface serving as a back side of the gripping surface of the probe treatment section 320 with respect to the center axis, and the probe treatment section 320 has a U-like cross-sectional shape. That is, a U-shaped bottom portion of the probe treatment section 320 faces the grip member 354.

A pad member 357 is provided on the grip member 354. The pad member 357 is made of a material having insulation properties, e.g., a fluororesin. In a state that the treatment section 360 is closed, the probe treatment section 320 comes into contact with the pad member 357, and a gap is formed between the probe treatment section 320 and the grip member 354. During use of the treatment apparatus 20, when the treatment section 360 grips the biological tissue and a high-frequency voltage is applied, a current flows through the biological tissue placed in the gap portion where the probe treatment section 320 faces the grip member 354. That is, the probe treatment section 320 and the grip member 354 function as a bipolar electrode. As a result, the biological tissue is sealed or coagulated at the portion through which the current has flowed. When the ultrasonic vibrator 310 vibrates, the probe treatment section 320 vibrates in its longitudinal axis direction, and the biological tissue is rubbed against the probe treatment section 320 and cut at the portion sandwiched between the probe treatment section 320 and the grip member 354.

Figure 25:
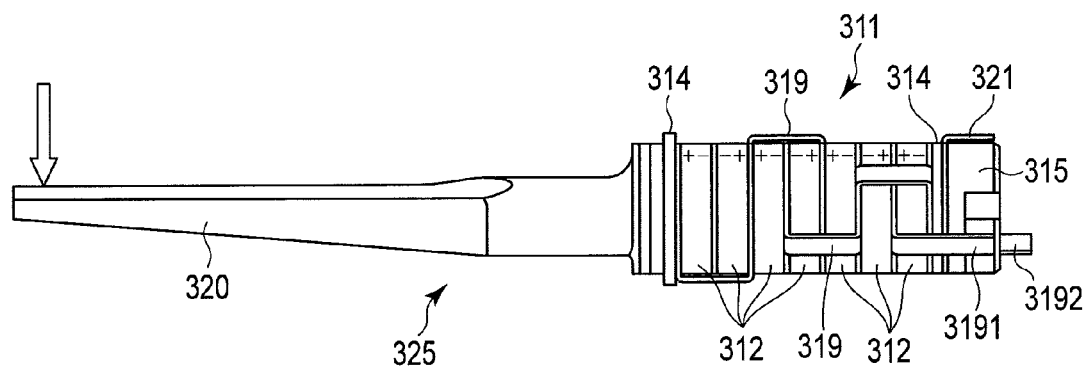
FIG. 25 is a view showing an outline of a structural example of an ultrasonic vibrator according to a third embodiment.
Figure 26:
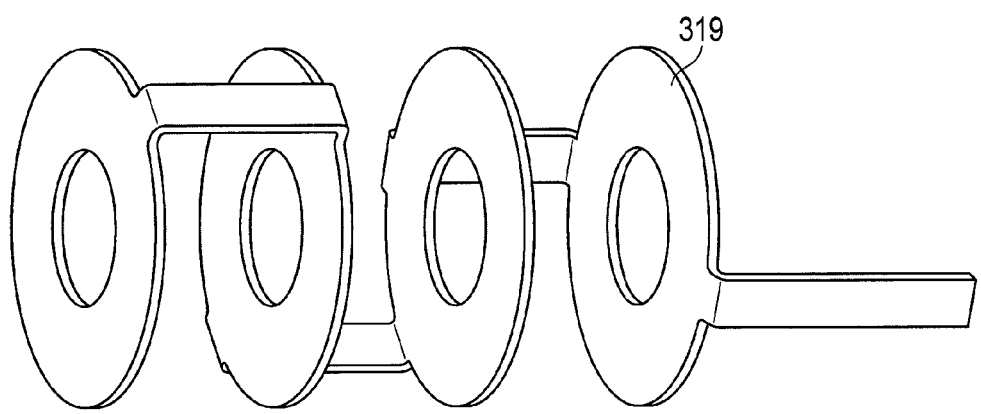
FIG. 26 is a view showing an outline of a structural example of an electrode member according to the third embodiment.

The vibration member 311 of the ultrasonic vibrator 310 will be further described with reference to FIG. 25 and FIG. 26. FIG. 26 is a perspective view of an electrode member 319 constituting the electrode 313 provided at each of both ends of each piezoelectric element 312 of the ultrasonic vibrator 310. As shown in FIG. 25, in the ultrasonic vibrator 310, two electrode members 319 are provided in a staggered manner. An end portion of one electrode member 319 is assumed to a positive electrode 3191, and an end portion of the other electrode member 319 is assumed to a negative electrode 3192. When a voltage is applied between the positive electrode 3191 and the negative electrode 3192, for example, such a voltage as shown in FIG. 25 is applied to both ends of each piezoelectric element 312. When an alternating-current voltage having a frequency corresponding to the ultrasonic wave is applied to both the ends of each piezoelectric element 312, each piezoelectric element 312 vibrates to generate the ultrasonic wave. Since the seven piezoelectric elements 312 are laminated, the ultrasonic vibrator 310 generates a large displacement.

Further, a high-frequency electrode 321 that is in contact with the ultrasonic transmission member 325 is provided between the insulating plate 314 and the lining plate 315. A high-frequency voltage is applied to the ultrasonic transmission member 325 through this high-frequency electrode 321. As shown in FIG. 25, the insulating plate 314 insulates the ultrasonic transmission member 325 from the electrode members 319.

FIG. 27 to FIG. 29 show dimensions of each section, e.g., the ultrasonic transmission member 325 or the like. FIG. 27 is a front view showing the ultrasonic transmission member 325 from the distal end side. As shown in this drawing, a width of the probe treatment section 320 is, e.g., 1.7 mm, and a width of the groove provided in the probe treatment section 320 is, e.g., 1.2 mm.

FIG. 28 is a side elevation of the ultrasonic transmission member 325 and others, and FIG. 29 is a cross-sectional view of the ultrasonic transmission member 325 and others. A distal end position of the probe treatment section 320 is determined as an origin, and a length toward a proximal end side is defined. A length of a grip section of the probe treatment section 320 facing the grip member 354 is 15 mm. A length from the distal end to the insulating plate 314 is, e.g., 27 mm. A length of the ultrasonic transmission member 325 is, e.g., 41 mm. A height of the probe treatment section 320 is gradually lowered toward the distal end. The gripping surface of the probe treatment section 320 facing the grip member 354 is parallel to a center axis of the ultrasonic transmission member 325 in the longitudinal direction. On the other hand, the back side of the probe treatment section 320 that is on the opposite side of the surface facing the grip member 354 is inclined, e.g., 4° with respect to the center axis. The height of the probe treatment section 320 at the distal end portion is, e.g., 1.4 mm, and the height of the probe treatment section 320 at the proximal end portion is 3.2 mm. A depth of the groove in the probe treatment section 320 at the proximal end portion is, e.g., 2.5 mm. A bottom portion of the groove is parallel to the center axis. An outer diameter of each piezoelectric element 312 is, e.g., 5 mm.

A dashed-two dotted line in FIG. 28 represents a vibration velocity of the ultrasonic vibration generated by the ultrasonic vibrator 310. In this embodiment, a node of the ultrasonic vibration is generated in the convex portion 327 where the ultrasonic transmission member 325 is in contact with the ultrasonic vibrator 310. As shown in FIG. 28, since the probe treatment section 320 is gradually thinned toward the distal end, the vibration velocity is increased toward the distal end.

Figure 30:
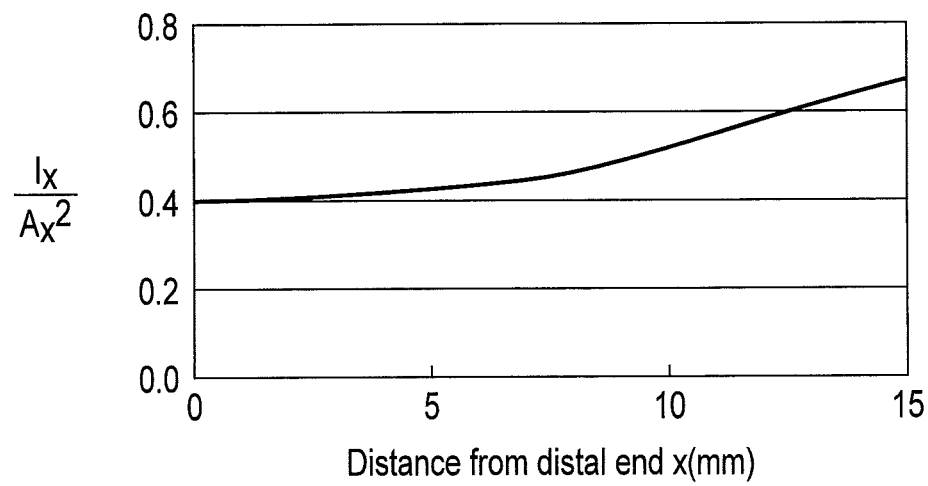
FIG. 30 is a view showing an example of a relationship between a distance of a probe treatment section from the distal end and a value obtained by dividing a second moment of area by a square of a cross-sectional area according to the third embodiment.

FIG. 30 shows a relationship between a distance x from the distal end and a value obtained by dividing a second moment of area $I_x$ by a square of a cross-sectional area $A_x$, i.e., $I_x/A_x^2$ in the probe treatment section 320 according to this embodiment. As shown in this drawing, $I_x/A_x^2$ gradually increases from the distal end side toward the proximal end side. Furthermore, at the most proximal position, $I_x/A_x^2$ becomes maximum. That is, the probe treatment section 320 according to this embodiment has rigidity per unit area that gradually increases from the distal end side toward the proximal end side, and the rigidity per unit area becomes maximum at the proximal end.

Figure 31:
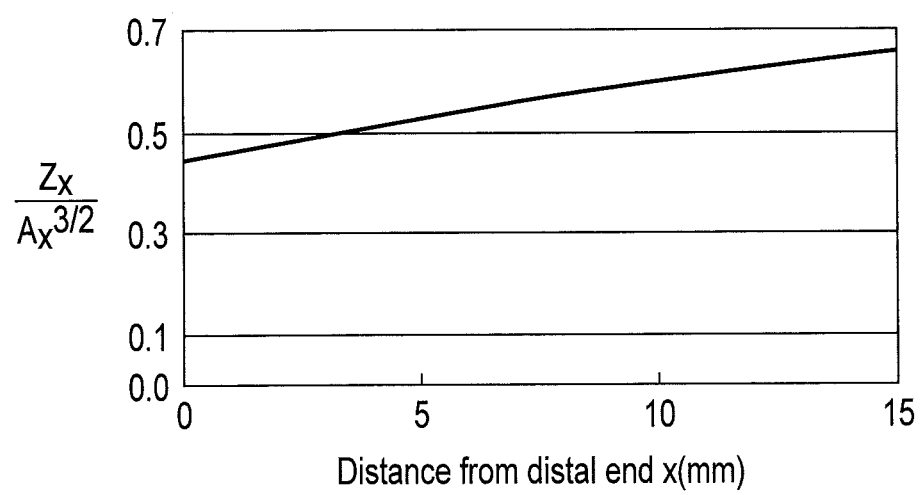
FIG. 31 is a view showing an example of a relationship between the distance of the probe treatment section from the distal end and a value obtained by dividing a section modulus by the 3/2 power of the cross-sectional area according to the third embodiment.

Furthermore, FIG. 31 shows a relationship between the distance x from the distal end and a value obtained by dividing a section modulus $Z_x$ by the 3/2 power of the cross-sectional area $A_x$, i.e., $Z_x/A_x^{3/2}$ in the probe treatment section 320. As shown in this drawing, $Z_x/A_x^{3/2}$ gradually increases from the distal end side toward the proximal end side. Moreover, $Z_x/A_x^{3/2}$ becomes maximum at the most proximal position. That is, in the probe treatment section 320 according to this embodiment, strength against bending per unit area is gradually increased from the distal end side toward the proximal end side, and the strength against bending per unit area becomes maximum at the proximal end.

When the probe treatment section 320 is formed into the shape as in this embodiment, $I_x/A_x^2$ is larger on the proximal end side than on the distal end side while maintaining appropriate cross-sectional areas, thereby making it difficult to bend on the proximal end side as compared to the distal end side. Further, as in this embodiment, $Z_x/A_x^{3/2}$ is larger on the proximal end side than on the distal end side, and the strength is higher on the proximal end side than on the distal end side. That is, according to this embodiment, sufficient difficulty in bending and sufficient strength can be assured while maintaining appropriate cross-sectional areas.

A modification of this embodiment will now be described with reference to FIG. 32 and FIG. 33. FIG. 32 shows a cross-sectional view of the ultrasonic vibrator 310 and the ultrasonic transmission member 325 according to this modification, and FIG. 33 shows a top view of the same. The probe treatment section 320 according to this modification has a thicker proximal end side than that of the probe treatment section 320 according to the third embodiment. Additionally, in the probe treatment section 320 according to this modification, the groove bottom portion is inclined relative to the center axis so that the U-shaped groove becomes deeper on the proximal end side.

When a configuration as in this modification is adopted, the proximal end side of the probe treatment section 320 becomes thick, hence stress caused due to a gripping load is distributed to lower the maximum stress applied to the probe treatment section 320. As a result, the probe treatment section 320 according to this modification becomes strong with respect to the gripping load. Further, since the U-shaped groove bottom portion is inclined with respect to the center axis and the groove is deep on the proximal end side, the cross-sectional area is gradually decreased toward the distal end portion of the probe treatment section 320, and the vibration velocity in the treatment section of the probe treatment section 320 is increased.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device comprising:
a first grip member having an elongated shape; and
a second grip member which comprises a grip section adapted to come into contact with a biological tissue as a gripping target and which is displaced with respect to the first grip member to grip the biological tissue between the first grip member and the second grip member, wherein an end of the grip section on a side connected with the first grip member is a proximal end; an end of the grip section on a free end side is a distal end; and $I/A^2$ of the grip section is maximum at the proximal end, and/or $Z/A^{3/2}$ of the grip section is maximum at the proximal end, where I is a second moment of area, Z is a section modulus, and A is a cross-sectional area calculated based on an axis perpendicular to a straight line passing through a center of gravity of the first grip member and a center of gravity of the second grip member in a cross section perpendicular to a longitudinal axis of the grip section, wherein
when the first grip member and the second grip member grip the biological tissue, the second grip member is configured to ultrasonically vibrate, and
a shape of the cross section of the grip section is an inverted U-shape in which a side opposite to a side facing the first grip member is open.

2. The treatment device according to claim 1, wherein $I/A^2$ of the grip section gradually increases from the distal end toward the proximal end, and/or $Z/A^{3/2}$ of the grip section gradually increases from the distal end toward the proximal end.

3. The treatment device according to claim 1, wherein
the first grip member and/or the second grip member is configured to apply a high-frequency voltage to the biological tissue.

4. The treatment device according to claim 1, wherein a cross-sectional area of the cross section of the grip section is larger at the proximal end than at the distal end.

5. The treatment device according to claim 1, wherein a density of a material forming a first region including the proximal end of the grip section is higher than a density of a material forming a second region other than the first region of the grip section.

6. The treatment device according to claim 5, wherein the first region includes a stainless steel, and the second region includes a titanium alloy.

7. The treatment device according to claim 1, wherein the second grip member is configured to ultrasonically vibrate.

8. The treatment device according to claim 1, wherein a first region including the proximal end of the grip section is provided with residual stress.

* * * * *